United States Patent [19]

Leone-Bay

[11] Patent Number: 4,711,962

[45] Date of Patent: * Dec. 8, 1987

[54] PROCESS FOR SELECTIVE PREPARATION OF RATIOS OF ISOMERS FORMED ON N-SUBSTITUTION OF ASYMMETRIC IMIDAZOLES

[75] Inventor: Andrea Leone-Bay, Ridgefield, Conn.

[73] Assignee: Stauffer Chemical Company, Westport, Conn.

[ * ] Notice: The portion of the term of this patent subsequent to Feb. 18, 2003 has been disclaimed.

[21] Appl. No.: 782,676

[22] Filed: Oct. 2, 1985

Related U.S. Application Data

[63] Continuation-in-part of Ser. No. 662,009, Oct. 18, 1984, Pat. No. 4,595,400, and a continuation-in-part of Ser. No. 730,964, May 6, 1985, Pat. No. 4,571,257.

[51] Int. Cl.$^4$ ............................................. C07D 233/90
[52] U.S. Cl. ..................................................... 548/337
[58] Field of Search ......................................... 548/337

[56] References Cited

U.S. PATENT DOCUMENTS 4,039,543  8/1977  Kompis et al. ...................... 544/325
4,571,257  2/1986  Leone-Bay et al. ................. 548/337

OTHER PUBLICATIONS

Grimmett, M., *Adv. Het. Chem.*, vol. 27, Academic Press, New York, 1980, pp. 288–297.
Grimmett, M., *Adv. Het. Chem.*, vol. 12, Academic Press, New York, 1970, p. 164.
Hofmann, K., *Imidazole and its Derivatives,* Part I, Interscience, New York, 1953, pp. 26–30.

*Primary Examiner*—Richard A. Schwartz

[57] ABSTRACT

Novel processes are disclosed for selectively preparing a mixture of certain asymmetric imidazole derivatives and their corresponding regioisomers. The process involves reacting a tautomeric mixture of two precursor compounds with a critical base in the presence of a critical solvent, prior to the desired N-substitution reaction. In general, the base is a hydride of an alkali metal or an alkaline earth metal, or mixtures thereof. Sodium hydride is particularly suitable. The solvents are all non-polar.

35 Claims, No Drawings

PROCESS FOR SELECTIVE PREPARATION OF RATIOS OF ISOMERS FORMED ON N-SUBSTITUTION OF ASYMMETRIC IMIDAZOLES

CROSS-REFERENCE TO RELATED APPLICATIONS

This is a continuation-in-part application of application Ser. No. 662,009, filed Oct. 18, 1984, now U.S. Pat. No. 4,595,400; and also a continuation-in-part application of application Ser. No. 730,964, filed May 6, 1985 now U.S. Pat. No. 4,571,257.

BACKGROUND

1. Field of the Invention

This invention relates generally to ratios of isomers formed on N-substitution of asymmetric imidazoles. More particularly, it relates to the preparation of novel compounds including some of those disclosed in both the aforementioned parents of this continuation-in-part application. It also relates to the novel mixtures thereby obtained, as well as to other related processes.

2. Related Art

There is extensive prior art relating to the tautomeric character of asymmetric imidazoles containing a free imino hydrogen (i.e. imidazoles containing a substituent in the 4- or 5-position, or two dissimilar substituents in these positions). There is also prior art relating to the ratio of isomers formed on methylation of imidazoles under varying conditions. For example, see *Imidazole and its derivatives* Part I by K. Hofmann, published by Interscience Publishers (1953), at pages 26–30 and also "Advances in Imidazole Chemistry" by M. R. Grimmett in *Advances in Heterocyclic Chemistry*, Volume 27, published by Academic Press (1980), at pages 288–297. However, such known prior art does not disclose the novel products claimed hereinafter nor the specific processes to make them.

Arthur C. Bayer's pending application Ser. No. 589,608, filed Mar. 14, 1984, discloses sodium salts of some asymmetric imidazoles (see page 3, middle of the page; Examples 23 and 26 in Table 1 at page 6; and all claims). However, Examples 23 and 26 do not indicate which particular sodium base was used to prepare the salts. Nor is any ratio given for the "two resonance forms Ia and IIa" on page 3 prepared by proton removal with "any" base.

The related art also includes descriptions of the preparation of imidazole derivatives in the presence of sodium hydride. However, all such references appear to be irrelevant because they relate to non-asymmetric imidazoles, etc.

Essentially, nowhere does the now-known prior art disclose or suggest the process claimed hereinafter wherein pairs of novel compounds are prepared in preselected ratios.

SUMMARY OF THE INVENTION

In contrast to the aforementioned prior art, there has now been discovered a novel process for selectively preparing a mixture of certain asymmetric imidazole derivatives and their corresponding regioisomers. The process involves reacting a tautomeric mixture of two precursor compounds with a critical base in the presence of a critical solvent, prior to the desired N-substitution reaction.

DESCRIPTION OF THE PREFERRED EMBODIMENTS

The preferred embodiments of the invention are described below with regard to (i) Typical Products; (ii) Preparation of Precursor Ester Compounds; and (iii) Selective N-Substitution Process. The Examples hereinafter exemplify the invention, but are not limitative thereof. The Comparative Examples hereinafter are not prior art.

N-substitution of an imidazole can be defined as any reaction process which places a substituent other than hydrogen on a nitrogen of an imidazole ring.

(i) Typical Products

This invention relates particularly to the selective preparation of certain regioisomers of esters of 2-bromo-4-methylimidazole-5-carboxylic acid. Such compounds are novel and have utility as herbicides, particularly the following compounds (hereinafter C3A) having the structural formula:

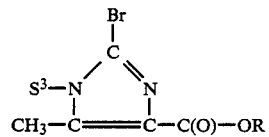

wherein:

$S^3$ is $C_1$–$C_{10}$ alkyl or $C_1$–$C_{10}$ allyl or cyanoethyl; or $C_1$–$C_{10}$ alkoxymethyl or $C_1$–$C_{10}$ thiomethyl or $C_1$–$C_{10}$ sulfoxymethyl or $C_1$–$C_{10}$ sulfonomethyl; and R is $C_2$–$C_{10}$ alkyl; $C_3$–$C_8$ cycloalkyl; $C_3$–$C_8$ cycloalkylalkyl, wherein the alkyl has 2 to 8 carbon atoms; allyl or 2-methyl-3-butenyl-1; $C_5$–$C_8$ cycloalkyl; benzyl or mono- or disubstituted benzyl, wherein the substituent is $C_1$–$C_4$ alkyl, halogen, nitro or $C_1$–$C_4$ haloalkyl.

Regioisomers of C3A (hereinafter C3B) also have some utility as herbicides, although in general at a much reduced level, and have the following structural formula:

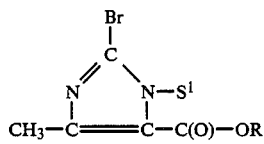

wherein:

R is as above; and $S^1$ is as $S^3$ above in C3A.

In the above description of the compounds made by this invention the term "alkyl" includes both straight and branched configurations; for example, methyl, ethyl, n-propyl, isopropyl, n-butyl, sec-butyl, isobutyl, and tertbutyl, the amyls, the hexyls, the heptyls, the nonyls and the decyls.

The following is a first table of certain selected compounds that are preparable according to the procedures described herein. The compounds are also disclosed in the parent application filed Oct. 18, 1984. Compound numbers are assigned to each compound for convenience.

TABLE IA

| Compound No. | R | S³ | m.p. °C. |
|---|---|---|---|
| 1[a] | i-propyl | i-propyl | yellow oil |
| 2 | sec-butyl | i-propyl | yellow oil |
| 3 | ethyl | cyclopropylmethyl | yellow oil |
| 4 | i-propyl | ethyl | yellow oil |
| 5 | n-propyl | i-propyl | yellow oil |
| 6[b] | i-propyl | methyl | 77–79 |
| 7 | sec-pentyl | methyl | dark oil |
| 8 | sec-butyl | methyl | dark oil |
| 9 | i-propyl | allyl | yellow oil |
| 10[c] | ethyl | methyl | 67–68 |

[a]Prepared in Comparative Example 2.
[b]Prepared in Examples 4A and 40 and Comparative Example 3A etc.
[c]Prepared in Example 4B and Comparative Example 3C etc.

The following is a second table of certain selected compounds that are preparable according to the procedures described herein. The compounds and methods for their preparation are also disclosed in the parent application, Ser. No. 730,964, filed May 6, 1985 now U.S. Pat. No. 4,571,257. Compound numbers are assigned to each compound for convenience. All of the compounds listed in the table below are yellow oils.

TABLE 1B

| Compound No. | R | S³ |
|---|---|---|
| 11 | i-propyl | methylthiomethyl |
| 12 | ethyl | methylthiomethyl |
| 13 | i-propyl | methylsulfonomethyl |
| 14 | i-propyl | methylsulfoxomethyl |
| 15 | i-propyl | 4-chlorophenylthiomethyl |
| 16 | i-propyl | phenylthiomethyl |
| 17[e] | i-propyl | phenylsulfonomethyl |
| 18 | i-propyl | methoxymethyl |
| 19 | i-propyl | n-propoxymethyl |
| 20[d] | i-propyl | n-butoxymethyl |
| 21 | i-propyl | s-butoxymethyl |
| 22 | i-propyl | i-propoxymethyl |

[d]Prepared in Example 8
[e]Prepared in Example 9

The C3A compounds made by this invention are active herbicides of a general type. This is, they are herbicidally effective against a wide range of plant species. The method of controlling undesirable vegetation of the present invention comprises applying a herbicidally effective amount of the above-described compounds to the area where control is desired.

(ii) Preparation of Precursor Ester Compounds

The precursor ester compounds of the present invention can be prepared by transesterification methods such as that shown in Example 1 (Precursor Preparation) below. In general the transesterification catalyst is Ti(O-alkyl)$_4$, preferably Ti(isopropoxy)$_4$. Also at least one mole of the alcohol is used for the reaction with the ethyl ester to prepare the imidazoles, Preferably, a slight mole excess of the alcohol is used. The reaction mixture is refluxed until completion of the reaction. The reaction product is recovered by removing the volatile materials. Atmospheric, subatmospheric or superatmospheric pressures can be used, depending on the boiling point of the solvent used. Ethanol is conveniently stripped at elevated temperatures and reduced pressure.

(iii) Selective N-Substitution Process

Reaction step (2) is run in a water-free solvent such as benzene or tetrahydrofuran or toluene, at a temperature of from about 25° C. to 100° C., preferably reflux temperature, using equal mole amounts of the two reactants and the base. Preferably, the metallic base is sodium hydride.

The reaction product includes a mixture of (1) and (3) isomers and is worked up by conventional techniques.

The (1) and (3) isomers can be separated by chromatography on silica gel, but this is often unnecessary for herbicidal applications. The (3) isomer which is the subject of this invention is the desired product. The (1) isomers have less herbicidal activity, and are not formed in major amounts according to the process of this invention.

The following Examples teach the synthesis of (1) and (3) isomers with the (3) isomer being present in a major amount. The following Comparative Examples gave products with the less desirable (1) isomer being present in a major amount.

Table 2 below summarizes the process conditions used in the Examples and Comparative Examples that relate to N-substitution. The following abbreviations have been used in Table 2: THF for tetrahydrofuran; DBU for diazabicycloundecane; and DBN for diazabicyclononane.

TABLE 2

PROCESS CONDITIONS

| Ex. No. | R | Base | Substituting Agent | Solvent | Temp. |
|---|---|---|---|---|---|
| Comp. 2 | i-Pr | DBU | 2-bromopropane | benzene | reflux |
| Comp. 3A | i-Pr | DBU | CH$_3$I | benzene | reflux |
| Comp. 3B | i-Pr | DBU | CH$_3$I | toluene | 25° C. |
| Comp. 3C | Et | DBU | CH$_3$I | toluene | 25° C. |
| Comp. 3D | Et | DBU | (CH$_3$O)$_2$SO$_2$ | toluene | 25° C. |
| Comp. 3E | Et | DBU | CH$_3$I | toluene | 38° C. |
| Comp. 3F | Et | DBU | CH$_3$I | toluene | 0° C. |
| Comp. 3G | Et | DBU | (CH$_3$O)$_2$SO$_2$ | toluene | 0° C. |
| Comp. 3H | Et | DBU | CH$_3$I | toluene | 0–25° C. |
| 4A | i-pr | NaH | CH$_3$I | THF | 25° C. |
| 4B | Et | NaH | CH$_3$I | THF | 25° C. |
| 4C | i-Bu | NaH | CH$_3$I | THF | 25° C. |
| Comp. 5 | i-Pr | DBN | CH$_3$I | benzene | reflux |
| Comp. 6 | i-Pr | triethylamine | CH$_3$I | benzene | reflux |
| Comp. 7 | i-Pr | DBU | 2-bromopropane | THF | 0–25° C. |
| 8 | i-Pr | NaH | methyl-n-butyl ether | THF | 0–25° C. |
| 9 | i-Pr | NaH | chloromethylphenylsulfoxide | THF | 0–25° C. |

The present invention is a process for selectively preparing a mixture of two compounds C3A and C3B, wherein C3A is a regioisomer of C3B and wherein C3A is an asymmetric imidazole derivative having the formula given before under the heading "(i) Typical Products" and C3B has the formula given before under the same title, which comprises the steps of reacting a tautomeric mixture of two compounds C1A and C1B with C1A having the formula C3A, with S³ being hydrogen, and C1B having the formula C1B, with S¹ being hydrogen, with an equimolar amount of a base, B, which is a hydride of an alkali metal or an alkaline earth metal, M, or mixtures thereof, in the presence of a non-polar solvent, S, thereby forming a mixture of two compounds C2A and C2B, wherein C2A is a salt of C1A and B and C2B is a salt of C1B and B, thereby forming a mixture of regioisomeric salts C2A, C2B, and hydrogen and then adding a preselected amount of an N-substituting agent ZS³, with Z being alkyl, aryl or sulfonyl and with $S^3$ being as earlier defined, the agent $ZS^3$ being an alkylating agent, an alkenylating agent or a cyanoethylating agent, to the mixture of regioisometric salts C2A and C2B, thereby forming a mixture of C3A and C3B in a ratio, r, of percentage amounts of C3A/C3B in the range of from 50/50 to 100/0 (e.g., wherein r is at least 60/40 or at least 70/30 or at least 80/20 or at least 90/10 or at least 95/5).

In the above, M can be a metal from Group IA or mixtures thereof such as sodium, potassium, lithium, or a metal from Group IIA or mixtures thereof, such as calcium, strontium, magnesium, barium. R can be a $C_1$-$C_5$ alkyl (isopropyl, n-butyl, t-butyl, iso-butyl, 1-methylbutyl, or methylpropyl), or $C_4$-$C_6$ cycloalkyl. R can be $C_3$-$C_5$ alkyl, $S^3$ can be $C_1$-$C_4$ alkyl (methyl, ethyl, isopropyl), cyclopropylmethyl, $C_3$-$C_6$ allyl or cyanoethyl. $S^3$ can be represented by $-CH_2-X-Y$ with X being sulfur, oxygen, sulfone or sulfoxide and with Y being phenyl, methyl, n-propyl, n-butyl, and isopropyl (e.g., $C_2$-$C_5$ alkyl groups).

Table 3 below summarizes data concerning the ratio of (3) isomer and (1) isomer obtained in the corresponding Examples and Comparative Examples.

TABLE 3

| | ISOMER RATIOS | |
|---|---|---|
| Ex. No. | (1) Isomer | (8) Isomer |
| Comp. 2 | 66 | 34 |
| Comp. 3A | 88 | 12 |
| Comp. 3B | 66 | 34 |
| Comp. 3C | 79 | 21 |
| Comp. 3D | 66 | 34 |
| Comp. 3E | 80 | 20 |
| Comp. 3F | 78 | 22 |
| Comp. 3G | 66 | 34 |
| Comp. 3H | 66 | 34 |
| 4A | 8 | 92 |
| 4B | 6 | 94 |
| 4C | 5 | 95 |
| Comp. 5 | 81 | 19 |
| Comp. 6 | 60 | 40 |
| Comp. 7 | 66 | 34 |
| 8 | 9 | 91 |
| 9 | 5 | 95 |

EXAMPLE 1 (PRECURSOR PREPARATION)

To a suspension of 6.4 grams (g) ($2.7 \times 10^{-2}$ moles) of ethyl 2-bromo-4-methyl-5-imidazole carboxylate in 70 milliliters (ml) isopropanol was added 0.6 ml ($2.4 \times 10^{-3}$ moles) tetraisopropyl titanate. The resulting mixture was heated to reflux for 3 days, then concentrated in vacuo to one-half the original volume. The solution was cooled on ice and the precipitated crystalline solid was filtered and air dried to give 3.4 g of the desired precursor tautomeric mixture of C1A and C1B wherein R was $CH(CH_3)_2$.

COMPARATIVE EXAMPLE 2

To a solution of 2 g ($8.1 \times 10^{-3}$ moles) of isopropyl 2-bromo-4-methyl-5-imidazolecarboxylate in 20 ml of benzene was added 1.2 ml ($8.2 \times 10^{-3}$ moles) of diazabicycloundecane, followed by 1.0 g. ($8.1 \times 10^{-3}$ moles) of 2-bromopropane. The resulting mixture was heated to reflux overnight, cooled to room temperature and filtered. Concentration in vacuo gave a golden oil. This residue was purified by medium pressure liquid chromatography on silica gel to yield 1.6 g (70%) isopropyl 1-isopropyl-2-bromo-4-methyl-5-imidazolecarboxylate as a yellow oil, but only 466 milligrams (20%) of the desired product, isopropyl 2-bromo-3-isopropyl-4-methyl-5-imidazolecarboxylate (also a yellow oil), wherein $S^1$ and $S^3$ and R were all $CH(CH_3)_2$.

COMPARATIVE EXAMPLES 3A-3H

The process of Comparative Example 2 was repeated except that the conditions used were modified as shown in Table 2. It will be noted that the base was kept the same (diazabicycloundecane), but that changes were made to the solvent and/or methylating agent and/or "R" and/or temperature. In each case, the product obtained was a mixture of regioisomers of the 1,4-dimethyl and 3,4-dimethyl types in an amount as shown in Table 3.

EXAMPLES 4A-4C

All of this group of Examples used sodium hydride as the base. Otherwise, the processing conditions were similar to those in Comparative Example 2A except for the changes noted in Table 2. The regioisomers were obtained in a mixture as shown in Table 3.

COMPARATIVE EXAMPLE 5

This Example was similar to Comparative Example 3A, except that the base was diazabicyclononane instead of diazabicycloundecane. The product contained 81% 1,4-dimethylregioisomer and 19% 3,4-dimethylregioisomer.

COMPARATIVE EXAMPLE 6

This Example was similar to Example 5 except that the base was triethylamine instead of diazabicycloundecane. The product contained C3A/C3B in a 40/60 ratio.

COMPARATIVE EXAMPLE 7

This Example was similar to Comparative Example 3A, except that the bromine substituent had been replaced by a hydrogen substituent. The purpose of the experiment was to determine whether the halogen atom affected the isomer ratio. Apparently it did not have a great effect, because the C3A/C3B ratio was relatively unchanged at 34/66.

EXAMPLE 8

To a suspension of 293 milligrams (1.22 mM) of sodium hydride in 30 ml of anhydrous tetrahydrofuran was added, in portions, 3 g (1.22 mM) of isopropyl 2-bromo-4-methyl-5-imidazolecarboxylate. The resulting suspension was cooled to 0° C. and 1.5 g (1.22 mM) of chloromethyl-n-butyl ether was added dropwise. The reaction mixture was stirred overnight at room temperature. The precipitated sodium chloride was removed by filtration and concentration of the filtrate in vacuo gave 3.6 g of isopropyl N-n-butoxymethyl-2-bromo-4-methyl-5-imidazolecarboxylate as a golden oil (87%). Subsequent analysis indicated that the 3-isomer/1-isomer ratio was 91/9.

EXAMPLE 9

To a suspension of 195 mg (8.13 mM) of sodium hydride in 20 ml of anhydrous tetrahydrofuran was added, in portions, 2 g (8.13 mM) of the isopropyl 2-bromo-4-methyl-5-imidazolecarboxylate. The resulting suspension was cooled to 0° C. and 1.4 g (8.13 mM) of chloromethylphenylsulfoxide was added by drop. The reaction mixture was stirred overnight at room temperature. The precipitated sodium chloride was removed by filtration and concentration of the filtrate in vacuo gave 3.1 g of isopropyl N-methylphenylsulfoxo-2-bromo-4-methyl-5-imidazolecarboxylate as a golden oil. Subsequent analysis indicated that the ratio 3-isomer/1-isomer was 95/5.

What I claim is:

1. A process for selectively preparing a mixture of two compounds C3A and C3B, wherein C3A is a regioisomer of C3B, and wherein C3A is an asymmetric imidazole derivative having the structural formula:

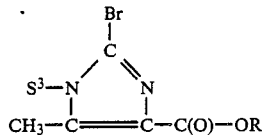

and C3B has the structural formula:

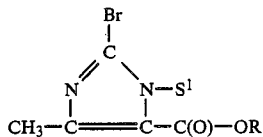

wherein:

$S^1$ or $S^3$ is $C_1-C_{10}$ alkyl or $C_3-C_{10}$ allyl or cyanoethyl; or $C_1-C_{10}$ alkoxymethyl or $C_1-C_{10}$ thiomethyl or $C_1-C_{10}$ sulfoxymethyl or $C_1-C_{10}$ sulfonomethyl; and R is $C_1-C_{10}$ alkyl; $C_3-C_8$ cycloalkyl; $C_3-C_8$ cycloalkylalkyl, wherein the alkyl has 2 to 8 carbon atoms; allyl or 2-methyl-3-butenyl-1; $C_5-C_8$ cycloalkyl; benzyl or mono- or disubstituted benzyl, wherein the substituent is $C_1-C_4$ alkyl, halogen, nitro or $C_1-C_4$ haloalkyl which comprises the steps of:

(1) reacting a tautomeric mixture of two compounds, C1A and C1B, with an equimolar amount of a base, B, in the presence of a solvent, S, thereby forming a mixture of two compounds C2A and C2B, wherein C2A is a salt of C1A and B; and C2B is a salt of C1B and B; and C1A has the structural formula:

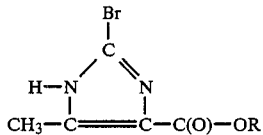

and C1B has the structural formula:

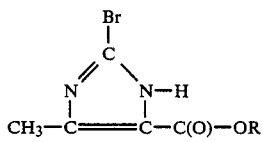

wherein:

R is as previously defined;

B is a hydride of an alkali metal or an alkaline earth metal, M, or mixtures thereof:

S is a tetrahydrofuran solvent;

thereby forming a mixture of regioisometric salts, C2A and C2B, and hydrogen; and then (2) adding a preselected amount of an N-substituting agent, $ZS^3$, selected from an alkylating agent, an alkenylating agent, or a cyanoethylating agent to the mixture of regioisometric salts C2A and C2B;

wherein:

$S^3$ is as previously defined; and,

Z is selected from alkyl, aryl, sulfonyl, alkoxyalkyl, benzyl, haloalkyl, and thioalkyl;

thereby forming a mixture of C3A and C3B in a ratio, r, of percentage amounts C3A/C3B within the range from 50/50 to 100/0.

2. The process of claim 1 wherein r is at least 95/5.

3. The process of claim 1 wherein M is an alkali metal from Group IA or mixtures thereof.

4. The process of claim 3 wherein M is selected from sodium, potassium, and lithium.

5. The process of claim 4 wherein M is sodium.

6. The process of claim 4 wherein M is potassium.

7. The process of claim 1 wherein M is an alkaline earth metal selected from Group IIA.

8. The process of claim 7 wherein M is selected from calcium, strontium, magnesium, and barium.

9. The process of claim 1 wherein R is $C_1-C_5$ alkyl or $C_4-C_6$ cycloalkyl.

10. The process of claim 9 wherein R is $C_3-C_5$ alkyl.

11. The process of claim 10 wherein R is isopropyl, n-butyl, t-butyl, iso-butyl, 1-methylbutyl or methylpropyl.

12. The process of claim 10 wherein R is isopropyl.

13. The process of claim 9 wherein R is isobutyl.

14. The process of claim 9 wherein R is n-butyl.

15. The process of claim 9 wherein R is t-butyl.

16. The process of claim 9 wherein R is 1-methylbutyl.

17. The process of claim 9 wherein R is 1-methylpropyl.

18. The process of claim 1 wherein $S^3$ is $C_1-C_4$ alkyl.

19. The process of claim 18 wherein $S^3$ is methyl.

20. The process of claim 18 wherein $S^3$ is ethyl.

21. The process of claim 18 wherein $S^3$ is isopropyl.

22. The process of claim 1 wherein $S^3$ is cyclopropylmethyl.

23. The process of claim 1 wherein $S^3$ is $C_3-C_6$ allyl.

24. The process of claim 1 wherein $S^3$ is cyanoethyl.

25. The process of claim 1 wherein X is selected from iodine, bromine and fluorine.

26. The process of claim 25 wherein X is iodine.

27. The process of claim 1 wherein the product comprises a mixture of C2A, C2B, C3A, and C3B.

28. The process of claim 1 wherein R is $C_2-C_5$ alkyl and $—S^3$ is capable of being represented by $—CH_2—X—Y$.

29. The process of claim 28 wherein R is isopropyl, X is sulfur and Y is phenyl.

30. The process of claim 28 wherein R is isopropyl, X is oxygen and Y is methyl.

31. The process of claim 28 wherein R is isopropyl, X is oxygen and Y is n-propyl.

32. The process of claim 28 wherein R is isopropyl, X is oxygen and Y is n-butyl.

33. The process of claim 28 wherein R is isopropyl, X is oxygen and Y is isopropyl.

34. The process of claim 28 wherein R is isopropyl, X is sulfone and Y is methyl.

35. The process of claim 29 wherein R is isopropyl, X is sulfoxide and Y is phenyl.

* * * * *